United States Patent
Bansal et al.

(10) Patent No.: US 11,426,235 B2
(45) Date of Patent: Aug. 30, 2022

(54) ELECTRODE LOOP ASSEMBLY INCLUDING SHAPED SUPPORT TUBE AND METHOD OF ASSEMBLING SAME

(71) Applicant: St. Jude Medical, Cardiology Division, Inc., St. Paul, MN (US)

(72) Inventors: Varun Bansal, Maple Grove, MN (US); Troy Tegg, Elk River, MN (US)

(73) Assignee: ST JUDE MEDICAL CARDIOLOGY DIVISION, INC, St. Paul, MN (US)

( * ) Notice: Subject to any disclaimer, the term of this patent is extended or adjusted under 35 U.S.C. 154(b) by 113 days.

(21) Appl. No.: 16/948,362

(22) Filed: Sep. 15, 2020

(65) Prior Publication Data

US 2021/0085385 A1    Mar. 25, 2021

Related U.S. Application Data

(60) Provisional application No. 62/902,699, filed on Sep. 19, 2019.

(51) Int. Cl.
*A61B 18/14*    (2006.01)

(52) U.S. Cl.
CPC .... *A61B 18/1492* (2013.01); *A61B 2018/144* (2013.01); *A61B 2018/1407* (2013.01)

(58) Field of Classification Search
CPC ........ A61B 18/1492; A61B 2018/1407; A61B 2018/144; A61B 5/287; A61B 2018/00577; A61B 5/6856; A61B 2017/00305; A61B 2017/00331; A61B 2017/00336; A61B 2017/0034; A61B 2017/00867; A61B 2018/00214; A61B 2018/00279; A61B 2018/1475; A61B 2034/301; A61B 5/6852; A61B 17/121; A61B 5/6851; A61M 25/0133; A61M 2025/015; A61M 25/09; A61M 25/0662; A61M 25/0152;

(Continued)

(56) References Cited

U.S. PATENT DOCUMENTS 6,071,274 A * 6/2000 Thompson ........ A61M 25/0141
                                                          604/533
6,233,476 B1    5/2001 Strommer et al.
(Continued)

FOREIGN PATENT DOCUMENTS

KR    20180070501 A * 6/2018 ........... A61B 17/221

OTHER PUBLICATIONS

International Search Report and Written Opinion for International Patent Application No. PCT/US2020/050817, dated Dec. 11, 2020, 12 pages.

*Primary Examiner* — Linda C Dvorak
*Assistant Examiner* — Mystee Nguyen Delgado
(74) *Attorney, Agent, or Firm* — Armstrong Teasdale LLP (57) ABSTRACT

An electrode loop assembly for a catheter includes a form wire shaped as a loop, an activation wire coupled to the form wire, and a support tube defining a lumen and enclosing the form wire and the activation wire therein. The activation wire is operable to selectively vary a diameter of the loop, and is routed along a radial inner side of the form wire. The support tube extends along a longitudinal axis from a proximal end to a distal end, and has an oblong cross-section having a major axis. The support tube is twisted about the longitudinal axis such that an orientation of the major axis changes along a length of the support tube.

20 Claims, 7 Drawing Sheets

(58) Field of Classification Search
CPC .......... A61M 25/0082; A61M 25/0009; A61M 25/01; A61M 2025/0163; A61M 2205/0266; A61M 25/00; A61M 5/00; A61M 2025/09066; A61M 25/09041
See application file for complete search history.

(56) References Cited

U.S. PATENT DOCUMENTS

| | | | |
|---|---|---|---|
| 6,332,880 B1 * | 12/2001 | Yang | A61B 18/1492 604/95.04 |
| 6,498,944 B1 | 12/2002 | Ben-Haim et al. | |
| 6,690,963 B2 | 2/2004 | Ben-Haim et al. | |
| 6,788,967 B2 | 9/2004 | Ben-Haim et al. | |
| 7,197,354 B2 | 3/2007 | Sobe | |
| 7,263,397 B2 | 8/2007 | Hauck et al. | |
| 7,386,339 B2 | 6/2008 | Strommer et al. | |
| 7,536,218 B2 | 5/2009 | Govari et al. | |
| 7,606,609 B2 * | 10/2009 | Muranushi | A61B 5/287 600/374 |
| 8,369,923 B2 * | 2/2013 | de la Rama | A61B 5/6856 600/374 |
| 9,387,035 B2 * | 7/2016 | Werneth | A61B 5/283 |
| 2003/0144657 A1 * | 7/2003 | Bowe | A61M 25/0133 606/41 |
| 2004/0059327 A1 | 3/2004 | Jenkins et al. | |
| 2005/0010095 A1 | 1/2005 | Stewart et al. | |
| 2008/0188850 A1 * | 8/2008 | Mody | A61B 18/1492 606/41 |
| 2017/0291008 A1 | 10/2017 | Hillukka et al. | |
| 2018/0177547 A1 | 6/2018 | Selkee et al. | |

\* cited by examiner

ELECTRODE LOOP ASSEMBLY INCLUDING SHAPED SUPPORT TUBE AND METHOD OF ASSEMBLING SAME

CROSS-REFERENCE TO RELATED APPLICATIONS

This application claims priority to U.S. provisional patent application Ser. No. 62/902,699, filed Sep. 19, 2019, the disclosure of which is hereby incorporated by reference in its entirety.

BACKGROUND OF THE DISCLOSURE a. Field of the Disclosure

The present disclosure relates generally to medical devices that are used in the human body. In particular, the present disclosure relates to electrode loop assemblies that include a shaped support tube configured to maintain a proper shape of the electrode loop assemblies.

b. Background

Medical devices, such as, for example, mapping, electroporation, and/or electrophysiology catheters, are used in a variety of diagnostic and/or therapeutic medical procedures including, for example, procedures to treat heart arrhythmias. Typically in a procedure, a catheter is manipulated through a patient's vasculature to a patient's heart, for example, and carries one or more electrodes that may be used for mapping, ablation, diagnosis, and/or to perform other functions. Once at an intended site, treatment may include radio frequency (RF) ablation, cryoablation, lasers, chemicals, high-intensity focused ultrasound, etc. As is readily apparent, such treatment requires precise control of the catheter during manipulation to, from, and at a mapping and/or treatment site, which can invariably be a function of a user's skill level.

Often, the catheter is inserted into an artery that is located a distance from the intended treatment site. For example, in procedures to treat heart arrhythmias, the catheter is typically inserted in the femoral artery, and the catheter must traverse a distance before reaching the heart. As such, the catheter must travel freely while preventing any possible surfaces of the catheter from catching or snagging on the interior surface of the blood vessels or other tissue. In catheters that include an electrode loop assembly, the loop assembly may be subjected to a variety of external forces while the catheter is traversing a patient's vasculature and/or during the procedure, and become deformed or misshaped as a result, making the electrode loop assembly more difficult to use.

SUMMARY OF THE DISCLOSURE

The present disclosure is directed to an electrode loop assembly for a catheter. The electrode loop assembly includes a form wire shaped as a loop, an activation wire coupled to the form wire, and a support tube defining a lumen and enclosing the form wire and the activation wire therein. The activation wire is operable to selectively vary a diameter of the loop, and is routed along a radial inner side of the form wire. The support tube extends along a longitudinal axis from a proximal end to a distal end, and has an oblong cross-section having a major axis. The support tube is twisted about the longitudinal axis such that an orientation of the major axis changes along a length of the support tube.

The present disclosure is further directed to a catheter assembly including a catheter shaft extending from a proximal end to a distal end, a handle coupled to the catheter shaft at the proximal end and including a loop actuator, and an electrode loop assembly coupled to the catheter shaft at the distal end thereof. The electrode loop assembly includes a form wire shaped as a loop, an activation wire coupled to the form wire and the loop actuator, and a support tube defining a lumen and enclosing the form wire and the activation wire therein. The activation wire is operable to selectively vary a diameter of the loop upon actuation of the loop actuator, and is routed along a radial inner side of the form wire. The support tube extends along a longitudinal axis from a proximal end to a distal end, and has an oblong cross-section having a major axis. The support tube is twisted about the longitudinal axis such that an orientation of the major axis changes along a length of the support tube.

The present disclosure is further directed to a method of assembling an electrode loop assembly. The method includes providing a form wire shaped as a loop, coupling an activation wire to the form wire such that the activation wire is operable to selectively vary a diameter of the loop, where the activation wire is routed along a radial inner side of the form wire, and routing the form wire and the activation wire through a lumen defined by a support tube, where the support tube defines a longitudinal axis and has an oblong cross-section having a major axis, and where the support tube is twisted about the longitudinal axis such that an orientation of the major axis changes along a length of the support tube.

DETAILED DESCRIPTION OF THE DISCLOSURE

The present disclosure is directed to medical devices including electrode loop assemblies for catheter systems, for use in the human vasculature for medical procedures such as mapping and/or ablation procedures, as well as methods of assembling the same. Electrode loop assemblies of the present disclosure include support tubes configured to maintain the proper shape of the electrode loop assemblies and prevent loop misshaping. For example, embodiments of support tubes disclosed herein are particularly suited to maintain the relative orientation of the form wire and the activation wire of an electrode loop assembly and, more specifically, are configured to constrain or confine the activation wire along the radial inner side of the form wire. By maintaining the relative orientation of the form wire and the activation wire, the support tubes described herein facilitate maintaining the proper shape of electrode loop assemblies in which they are implemented.

Embodiments of the support tubes described herein are specifically shaped to aid in maintaining the proper shape of electrode loop assemblies. For example, embodiments of the support tubes described herein have an oblong cross-section having a major axis, and are twisted about a longitudinal axis of the support tube such that an orientation of the major axis changes along a length of the support tube. The shape of support tubes described herein—for example, the twisted, oblong cross-sectional shape of the support tubes—facilitates maintaining the relative position of the activation wire and the form wire, and thereby facilitates maintaining the proper shape of electrode loop assemblies in which the support tubes are implemented. For example, the twisted, oblong cross-sectional shape of support tubes described herein inhibits the activation wire from moving radially past or outward from the form wire, and thereby confines the activation wire to the radial inner side of the form wire. Consequently, the support tubes of the present disclosure facilitate maintaining the proper shape of electrode loop assemblies and preventing loop misshaping.

Figure 1:
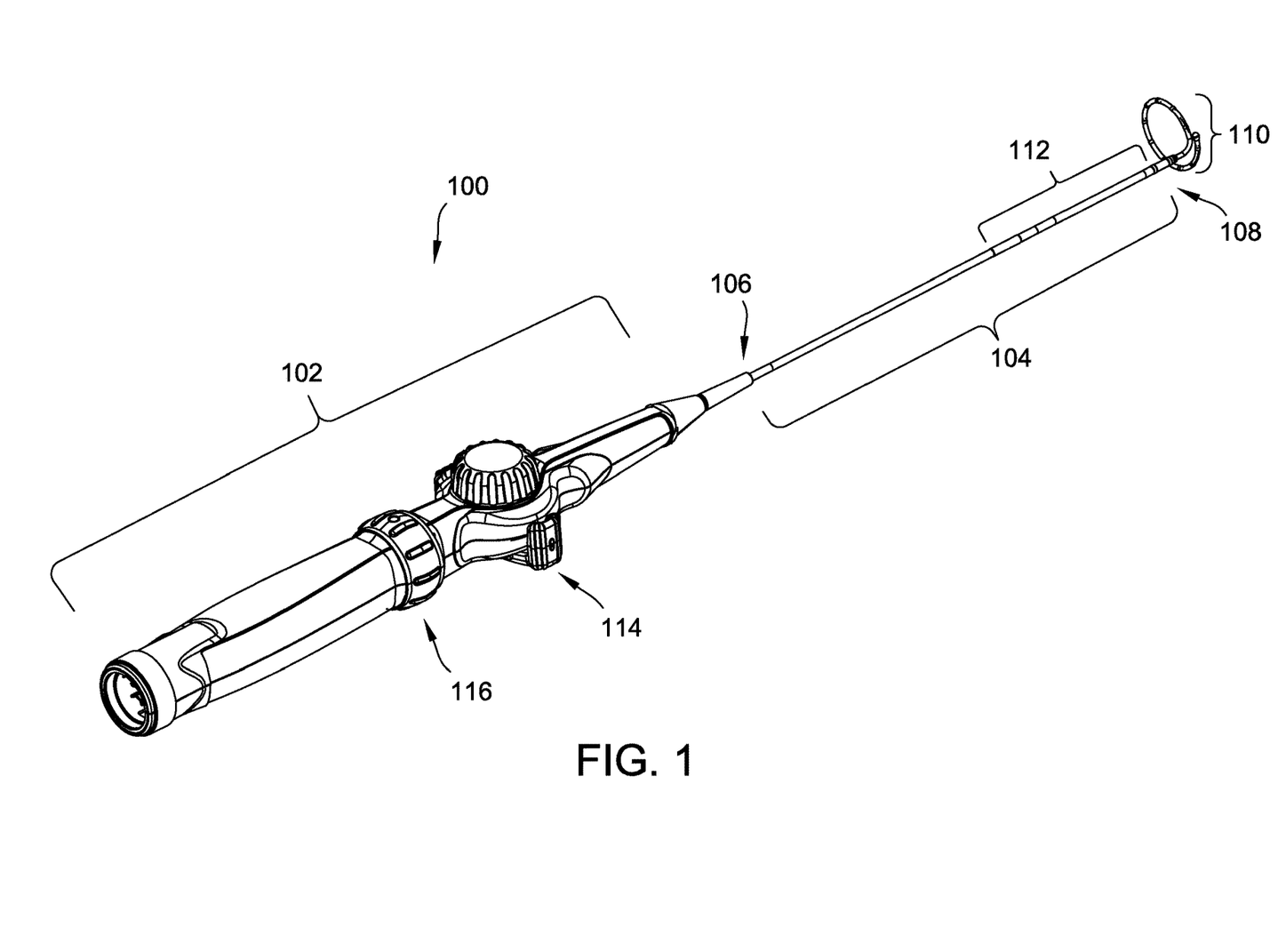
FIG. 1 is a perspective view of one embodiment of a catheter assembly including an electrode loop assembly.

Referring now to the drawings, FIG. 1 is an illustration of one embodiment of a catheter assembly 100 suitable for use with the electrode loop assemblies disclosed and described herein. Catheter assembly 100 includes a catheter handle 102 and a catheter shaft 104 extending from a proximal end 106 to a distal end 108. The distal end 108 of catheter shaft 104 includes an electrode loop assembly 110 coupled thereto. Various aspects of the electrode loop assembly are illustrated elsewhere herein, for example, FIGS. 3-6. Catheter assembly 100 may be used for mapping anatomic structures, as described herein. However, those of skill in the art will appreciate that the systems and methods described herein may also be implemented in other types of catheters (e.g., catheters used for ablation and/or electroporation).

Figure 2:
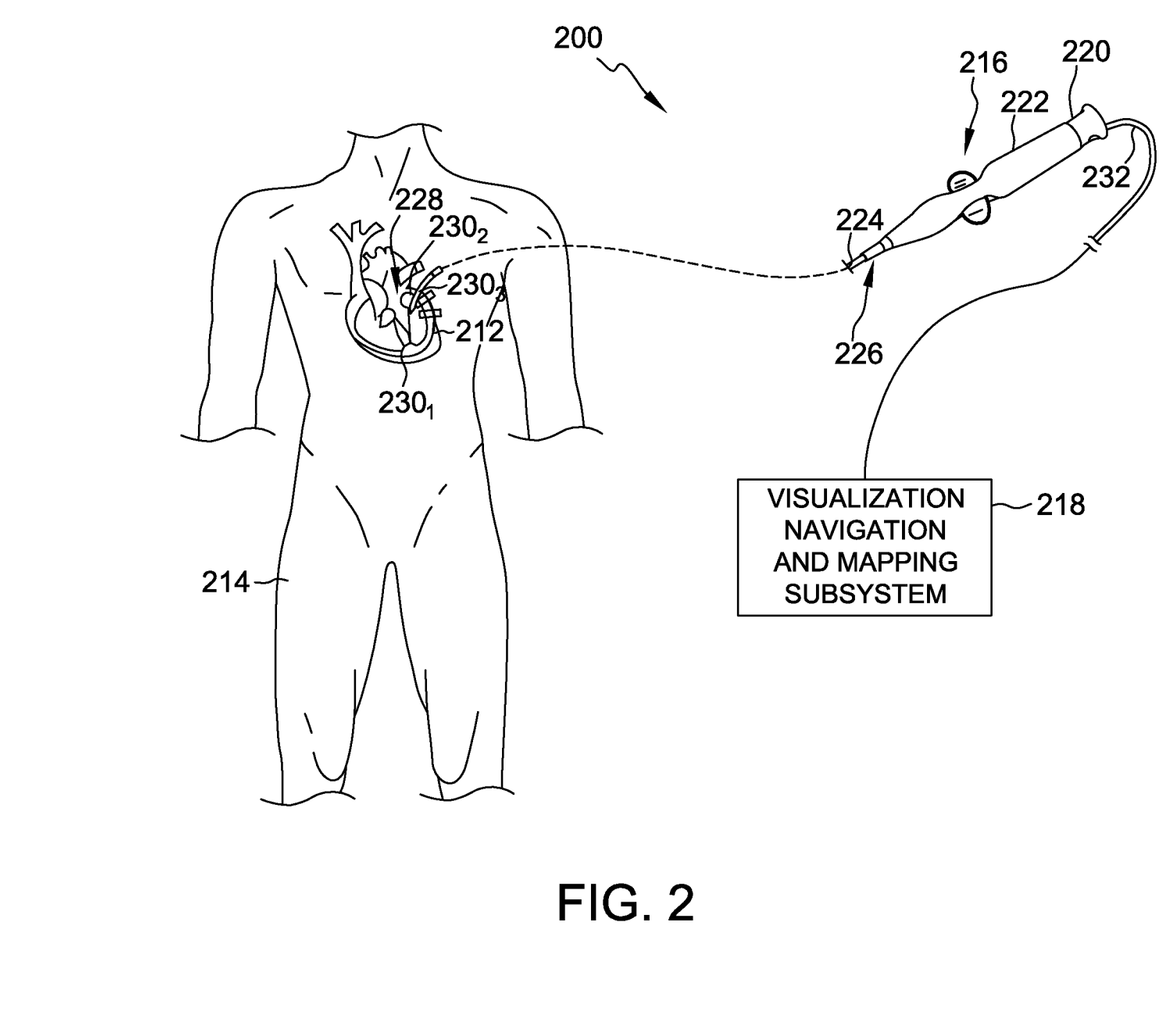
FIG. 2 is a schematic diagram of one embodiment of a system for performing one or more diagnostic and/or therapeutic functions that may use the catheter assembly shown in FIG. 1.

FIG. 2 illustrates one exemplary embodiment of a system 200 for performing one or more diagnostic and/or therapeutic functions on or for a tissue 212 of a body 214. System 200 may use, for example, catheter assembly 100 (shown in FIG. 1). In an exemplary embodiment, tissue 212 includes heart or cardiac tissue within a human body 214. It should be understood, however, that system 200 may find application in connection with a variety of other tissues within human and non-human bodies, and therefore, the present disclosure is not meant to be limited to the use of system 200 in connection with only cardiac tissue and/or human bodies.

System 200 may include a medical device (e.g., a catheter assembly 216) and a subsystem 218 for the visualization, navigation, and/or mapping of internal body structures (hereinafter referred to as the "visualization, navigation, and mapping subsystem 218", "subsystem 218", or "mapping system").

In this embodiment, medical device includes a catheter assembly 216, such as, for example, an electrophysiology catheter. In other exemplary embodiments, medical device may take a form other than catheter assembly 216, such as, for example and without limitation, a sheath or catheter-introducer, or a catheter other than an electrophysiology catheter. For clarity and illustrative purposes only, the description below will be limited to embodiments of system 200 wherein medical device is a catheter (catheter assembly 216).

Catheter assembly 216 is provided for examination, diagnosis, and/or treatment of internal body tissues such as tissue 212. Catheter assembly 216 may include a cable connector 220 or interface, a handle 222, a shaft 224 extending from a proximal end 226 to a distal end 228 (as used herein, "proximal" refers to a direction toward the end of catheter assembly 216 near handle 222, and "distal" refers to a direction away from handle 222), and one or more sensors, such as, for example and without limitation, a plurality of electrodes 230 (i.e., $230_1$, $230_2$, ..., $230_N$), mounted in or on shaft 224 of catheter assembly 216 at or near distal end 228 of shaft 224. Distal end 228 of catheter assembly 216 may include an electrode loop assembly, such as electrode loop assembly 110 (shown in FIG. 1).

In other embodiments, catheter assembly 216 may further include other conventional components such as, for example and without limitation, steering and activation wires and associated actuators, irrigation lumens and ports, pressure sensors, contact sensors, temperature sensors, additional electrodes and corresponding conductors or leads, and/or ablation elements (e.g., ablation electrodes, high intensity focused ultrasound ablation elements, and the like).

Connector 220 provides mechanical and electrical connection(s) for one or more cables 232 extending, for example, from visualization, navigation, and mapping subsystem 218 to one or more sensors mounted on catheter assembly 216. In other embodiments, connector 220 may also provide mechanical, electrical, and/or fluid connections for cables extending from other components in system 200, such as, for example, an ablation system and a fluid source (when catheter assembly 216 includes an irrigated catheter). Connector 220 is disposed at proximal end 226 of catheter assembly 216.

Handle 222 provides a location for a user to hold catheter assembly 216 and may further provide means for steering or guiding shaft 224 within body 214. For example, handle 222 may include means to manipulate one or more steering wires extending through catheter assembly 216 to distal end 228 of shaft 224 to steer shaft 224. It will be appreciated by those of skill in the art that the construction of handle 222 may vary. In other embodiments, the control of catheter assembly 216 may be automated such as by being robotically driven or controlled, or driven and controlled by a magnetic-based guidance system. Accordingly, catheters controlled either manually or automatically are both within the spirit and scope of the present disclosure.

Shaft 224 is an elongate, tubular, and flexible member configured for movement within body 214. Shaft 224 supports, for example and without limitation, electrodes 230, associated conductors, and possibly additional electronics used for signal processing or conditioning. Shaft 224 may also permit transport, delivery and/or removal of fluids (including irrigation fluids, cryogenic ablation fluids, and body fluids), medicines, and/or surgical tools or instruments. Shaft 224, which may be made from conventional materials such as polyurethane, defines one or more lumens configured to house and/or transport electrical conductors, fluids, or surgical tools. Shaft 224 may be introduced into a blood vessel or other structure within body 214 through a conventional introducer. Shaft 224 may then be steered or guided through body 214 to a desired location such as tissue 212. Distal end 228 of shaft 224 may be the main portion of catheter assembly 216 that contains electrodes 230 or other sensors for acquiring positioning data.

Visualization, navigation, and mapping subsystem 218 may be used to determine the positions of electrodes 230 or other sensors. These positions may be projected onto a geometrical anatomical model. In some embodiments, visualization, navigation, and mapping subsystem 218 includes a magnetic field-based system. For example, visualization, navigation, and mapping subsystem 218 may include an electrical field- and magnetic field-based system such as the ENSITE PRECISION™ system commercially available from Abbott Laboratories, and generally shown with reference to U.S. Pat. No. 7,263,397 entitled "Method and Apparatus for Catheter Navigation and Location and Mapping in the Heart", the entire disclosure of which is incorporated herein by reference. In such embodiments, distal end 228 may include at least one magnetic field sensor—e.g., magnetic coils (not shown). If two or more magnetic field sensors are utilized, a full six-degree-of-freedom registration of magnetic and spatial coordinates could be accomplished without having to determine orthogonal coordinates by solving for a registration transformation from a variety of positions and orientations. Further benefits of such a configuration may include advanced dislodgement detection and deriving dynamic field scaling since they may be self-contained.

In other exemplary embodiments, subsystem 218 may utilize systems other than electric field-based systems. For example, subsystem 218 may include a magnetic field-based system such as the CARTO™ system commercially available from Biosense Webster, and as generally shown with reference to one or more of U.S. Pat. No. 6,498,944 entitled "Intrabody Measurement"; U.S. Pat. No. 6,788,967 entitled "Medical Diagnosis, Treatment and Imaging Systems"; and U.S. Pat. No. 6,690,963 entitled "System and Method for Determining the Location and Orientation of an Invasive Medical Instrument," the disclosures of which are incorporated herein by reference in their entireties.

In yet another exemplary embodiment, subsystem 218 may include a magnetic field-based system such as the GMPS system commercially available from MediGuide Ltd., and as generally shown with reference to one or more of U.S. Pat. No. 6,233,476 entitled "Medical Positioning System"; U.S. Pat. No. 7,197,354 entitled "System for Determining the Position and Orientation of a Catheter"; and U.S. Pat. No. 7,386,339 entitled "Medical Imaging and Navigation System," the disclosures of which are incorporated herein by reference in their entireties.

In a further exemplary embodiment, subsystem 218 may utilize a combination electric field-based and magnetic field-based system as generally shown with reference to U.S. Pat. No. 7,536,218 entitled "Hybrid Magnetic-Based and Impedance Based Position Sensing," the disclosure of which is incorporated herein by reference in its entirety. In yet still other exemplary embodiments, the subsystem 218 may comprise or be used in conjunction with other commonly available systems, such as, for example and without limitation, fluoroscopic, computed tomography (CT), and magnetic resonance imaging (MRI)-based systems.

Although not shown in FIG. 2, in some embodiments, system 200 may include suitable components to perform electroporation and/or ablation (e.g., RF ablation). It should be understood that in such embodiments, variations are possible as to the type of ablation energy provided (e.g., cryoablation, ultrasound, etc.).

Referring back to FIG. 1, catheter shaft 100 includes a distal portion 112 and electrode loop assembly 110 coupled at the distal end 108 of catheter shaft 104. In some embodiments, distal portion 112 of catheter shaft 104 is deflectable in one or more directions, for example, to facilitate steering the catheter shaft 104 through the vasculature of a patient. Further, in some embodiments, a diameter of electrode loop assembly 110 is variable.

In at least some embodiments where catheter shaft 104 includes deflectable distal portion 112, catheter assembly 100 includes a shaft actuator 114 to allow an operator to selectively deflect distal portion 112 of catheter shaft 104. Further, in at least some embodiments where the diameter of electrode loop assembly 110 is variable, catheter assembly 100 includes a loop actuator 116 to allow an operator to adjust the diameter of electrode loop assembly 110; that is, an actuator to increase or decrease the diameter of electrode loop assembly 110. This diameter adjustment of electrode loop assembly 110 may be done at any time during a procedure, and may further be done with or without deflection of the distal end of catheter assembly 100; that is, any deflection of the distal end is independent of any diameter adjustment of electrode loop assembly 110 in accordance with the present disclosure. This independent adjustment may be achieved through the use of multiple pull or activation wires contained within catheter assembly 100, for example, as described in U.S. Pat. App. Pub. No. 2017/0291008 entitled "Mapping Variable Loop Catheter Handle", the disclosure of which is incorporated herein by reference in its entirety. By having the capability to adjust the diameter of electrode loop assembly 110 before or during a procedure, an operator may be able to more effectively navigate the vasculature of a patient and improve patient outcomes.

Figure 3:
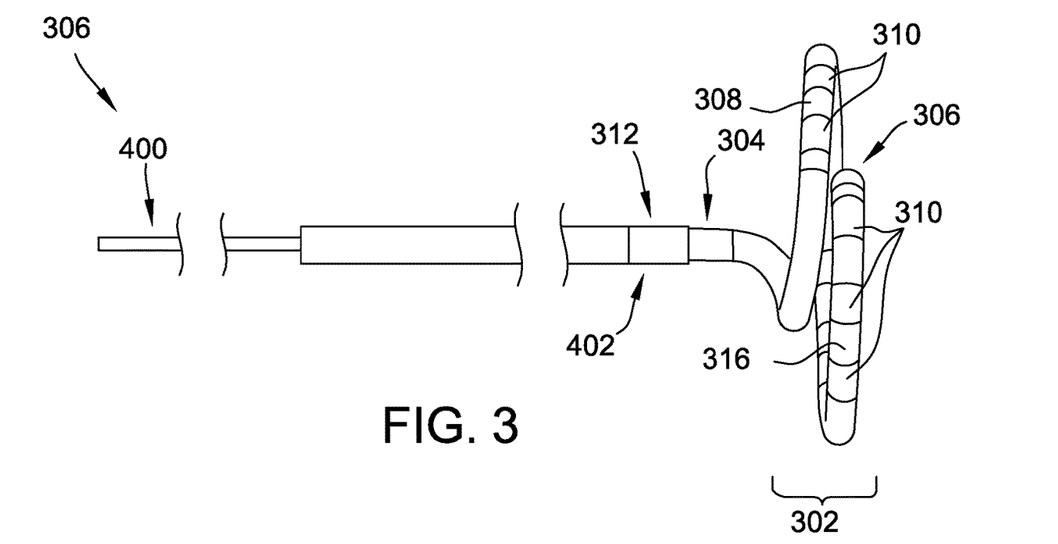
FIG. 3 is a side view of an electrode loop assembly that may be used with the catheter assembly shown in FIG. 1.
Figure 4:
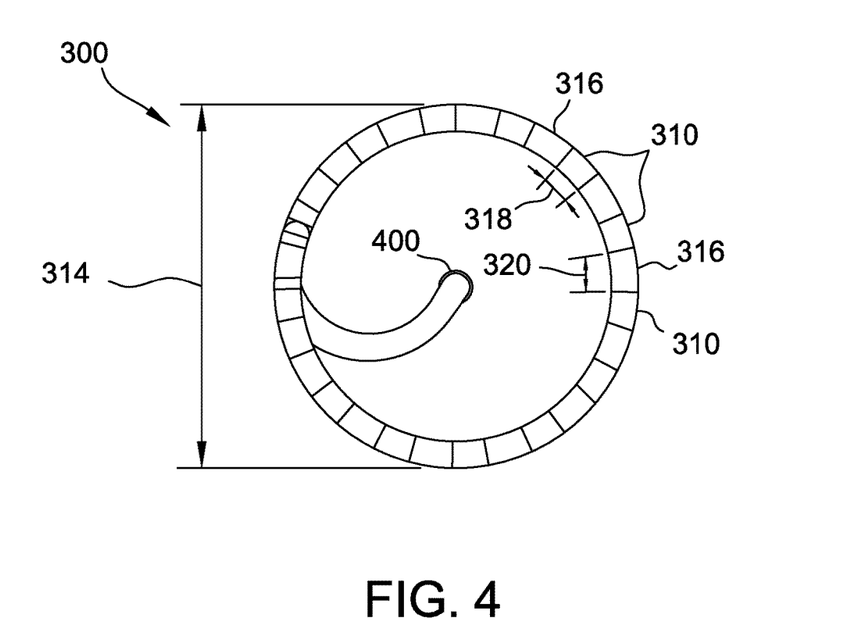
FIG. 4 is an end view of the electrode loop assembly of FIG. 3.

FIGS. 3 and 4 illustrate an electrode loop assembly 300 that may be used, in some embodiments, with catheter assembly 216 (shown in FIG. 2) and/or catheter assembly 100 (shown in FIG. 1). Specifically, FIG. 3 is a side view of electrode loop assembly 300 with a variable diameter loop 302 coupled at the distal end 402 of a catheter shaft 400. FIG. 4 is an end view of variable diameter loop 302 of electrode loop assembly 300.

As shown in FIGS. 3 and 4, electrode loop assembly 300 extends from a proximal end 304 to a distal end 306, and includes an outer sleeve 308 formed in the shape of a loop, and a plurality of catheter electrodes 310 mounted on outer sleeve 308. Proximal end 304 of electrode loop assembly 300 is coupled to catheter shaft 400 via a suitable coupler 312. Electrodes 310 may be used for a variety of diagnostic and therapeutic purposes including, for example and without limitation, cardiac mapping and/or ablation. For example, one or more of catheter electrodes 310 may perform a location or position sensing function. More particularly, one or more of catheter electrodes 310 may be configured to be a positioning sensor(s) that provides information relating to the location (position and orientation) of electrode loop assembly 300.

Variable diameter loop 302 is located at distal end 402 of catheter shaft 400 and has a diameter 314 transitionable between an expanded (also referred to as "open") diameter (shown in FIG. 4) and a retracted (also referred to as "closed") diameter (not shown). In the example embodiment, the expanded diameter is approximately twenty seven mm and the retracted diameter is approximately fifteen mm.

In other embodiments, diameter 314 may be variable between any suitable open and closed diameters.

In this embodiment, variable diameter loop 302 includes fourteen catheter electrodes 310 evenly spaced around the circumference of variable diameter loop 302. In other embodiments, variable diameter loop 302 may include any suitable number of catheter electrodes 310 made of any suitable material. Each catheter electrode 310 is separated from each other catheter electrode by an insulated gap 316. In the example embodiment, each catheter electrode 310 has a same length 318 (shown in FIG. 4) and each insulated gap 316 has a same length 320 as each other gap 316. Length 318 and length 320 are both about 2.5 mm in the example embodiment. In other embodiments, length 318 and length 320 may be different from each other. Moreover, in some embodiments, catheter electrodes 310 may not all have the same length 318 and/or insulated gaps 316 may not all have the same length 320. In some embodiments, catheter electrodes 310 are not spaced evenly around the circumference of variable diameter loop 302.

Figure 5:
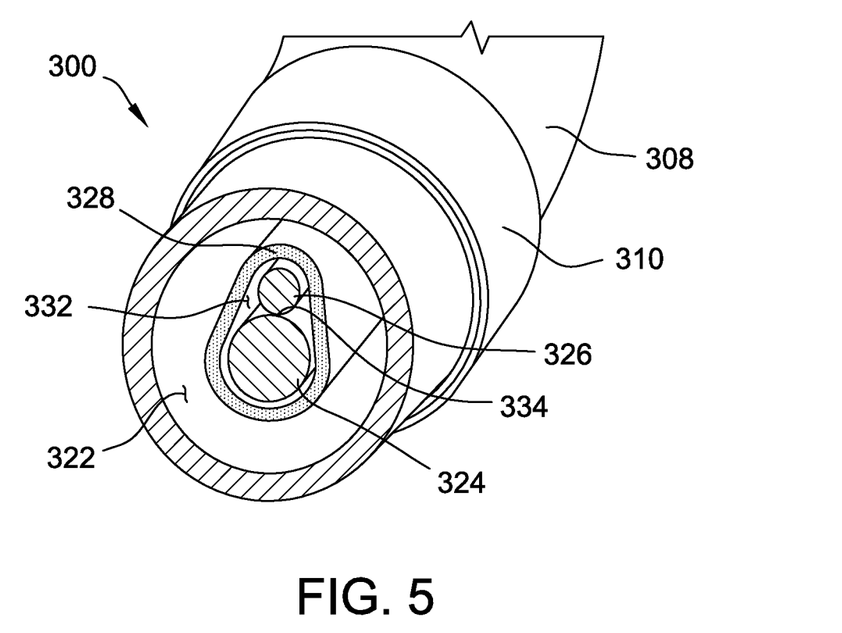
FIG. 5 is a cut-away view of the electrode loop assembly shown in FIGS. 3 and 4.
Figure 6:
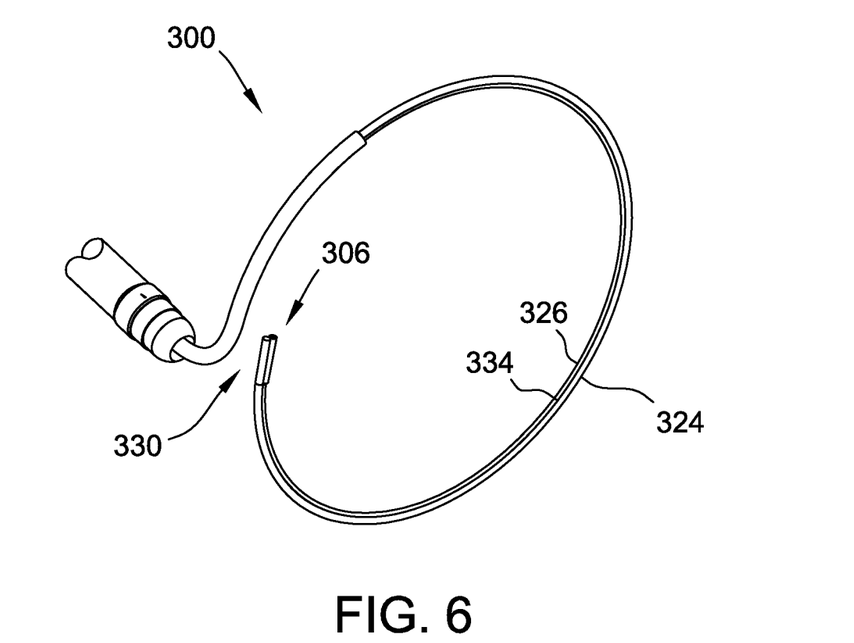
FIG. 6 is a perspective view of the electrode loop assembly of FIGS. 3-5 with portions of the electrode loop assembly omitted to show underlying features of the electrode loop assembly.

FIG. 5 is a cut-away view of electrode loop assembly 300 shown in FIGS. 3 and 4. As shown in FIG. 5, outer sleeve 308 of electrode loop assembly 300 defines a first or outer lumen 322. The outer lumen 322 is defined along substantially the entire length of electrode loop assembly 300 in the illustrated embodiment. Electrode loop assembly 300 also includes a form wire 324, an activation wire 326, and a support tube 328 positioned within outer lumen 322 and enclosed within outer sleeve 308. FIG. 6 is a perspective view of electrode loop assembly 300 with portions of electrode loop assembly 300 omitted (e.g., outer sleeve 308 and support tube 328) to show underlying features of electrode loop assembly 300.

Form wire 324 is shaped as a loop, and provides structural support to electrode loop assembly 300 to maintain the general shape of loop 302. Form wire 324 may be constructed from any suitable material that enables electrode loop assembly 300 to function as described herein including, for example and without limitation, stainless steel, copper-aluminum-nickel alloys, nickel-titanium (NiTi) alloys, nitinol, alloys including zinc, copper, gold, and/or iron, polymers including any of the above materials, and/or combinations thereof. In one specific embodiment of the present disclosure, form wire 324 is constructed from a memory-shape alloy, such as a nickel-titanium metal alloy. Such memory-shape alloys tend to have a temperature induced phase change that will cause the material to have a preferred configuration that can be fixed by heating the material above a certain transition temperature to induce a change in the phase of the material. When the alloy is cooled back down, the alloy will "recall" the shape it was in during the heat treatment and will tend to assume that configuration unless constrained from doing so. One particularly desirable memory shape alloy for use in the present disclosure is Nitinol, an approximately stoichiometric alloy of nickel and titanium, which may also include minor amounts of other metals to achieve desired properties. Nickel-titanium alloys are very elastic and are commonly referred to as "superelastic" or "pseudoelastic."

Activation wire 326 is coupled to form wire 324 at a distal end 330 thereof, and is operable to selectively vary a diameter of loop 302. For example, activation wire 326 may extend from distal end 306 of electrode loop assembly 300, through catheter shaft 400, and be coupled to a suitable loop actuator (e.g., loop actuator 116). In such embodiments, actuation of the loop actuator causes activation wire 326 to vary a diameter of loop 302, for example, by expanding or contracting loop 302.

Activation wire 326 may be coupled to form wire 324 using any suitable coupling method that enables electrode loop assembly 300 to function as described herein, including, for example and without limitation, welding, brazing, and combinations thereof. In the illustrated embodiment, activation wire 326 is coupled to form wire 324 only at distal end 330 of form wire 324. That is, activation wire 326 is coupled to form wire 324 at distal end 330 of form wire 324, and decoupled from form wire 324 along the remaining length of activation wire 326. Coupling activation wire 326 to form wire 324 only at distal end 330 of form wire 324 facilitates transitioning or changing the diameter of loop 302, for example, upon actuation of a suitable loop actuator (e.g., loop actuator 116).

Support tube 328 defines a second or inner lumen 332, and encloses form wire 324 and activation wire 326 therein. In the exemplary embodiment, support tube 328 has an oblong cross-section, specifically, an oval-shaped cross-section. In other embodiments, support tube 328 may have an oblong cross-section other than an oval-shaped cross-section, including, for example and without limitation, an elliptical cross-section and a pseudo-rectangular cross-section (i.e., a rectangle with rounded corners). Support tube 328 is constructed from a suitably resilient, flexible material such that support tube 328 maintains the relative orientation of form wire 324 and activation wire 326, yet still permits sufficient movement of form wire 324 and activation wire 326 to allow the diameter of loop 302 to be selectively varied. Suitable materials from which support tube 328 may be constructed include, for example and without limitation, braided materials, coiled wire, and combinations thereof. In one specific embodiment of the present disclosure, support tube 328 is constructed from a polyimide braided material.

Figure 11:
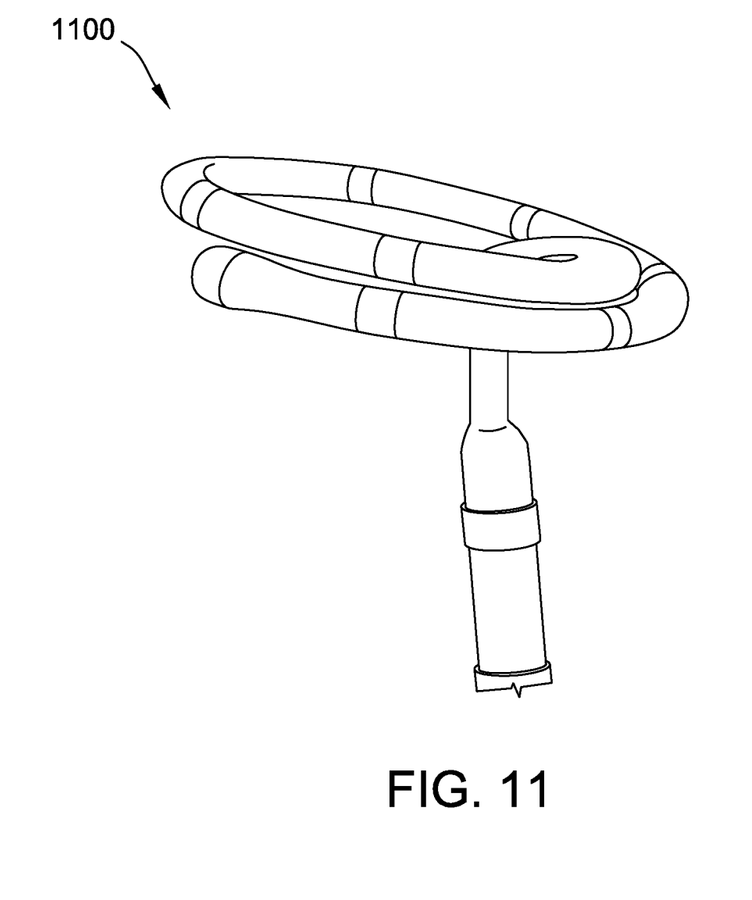
FIG. 11 is a perspective view of a misshaped electrode loop assembly.

As shown in FIGS. 5 and 6, activation wire 326 is routed along a radial inner side 334 of form wire 324. Support tubes of the present disclosure are particularly suited to maintain the relative orientation of form wire 324 and activation wire 326, for example, during use of a catheter assembly including electrode loop assembly 300. In particular, support tubes of the present disclosure are configured to constrain or confine activation wire 326 along radial inner side 334 of form wire 324. By maintaining the relative orientation of form wire 324 and activation wire 326, the support tubes described herein facilitate maintaining the proper shape of electrode loop assembly 300 and prevent loop misshaping, such as non-circular loops, pretzel loops, and loop diving. In particular, if activation wire 326 is allowed to move radially outward of form wire, activation wire may wrap around form wire 324 and apply non-planar forces (i.e., forces out of the plane in which loop 302 is situated) to distal end 330 of form wire 324, thereby causing loop misshaping, such as by loop diving. FIG. 11, for example, illustrates an electrode loop assembly 1100 in which an activation wire (not shown in FIG. 11) of the electrode loop assembly 1100 wrapped around the form wire (not shown in FIG. 11) of the electrode loop assembly 1100, and thereby caused misshaping of the electrode loop assembly 1100.

Figure 7:
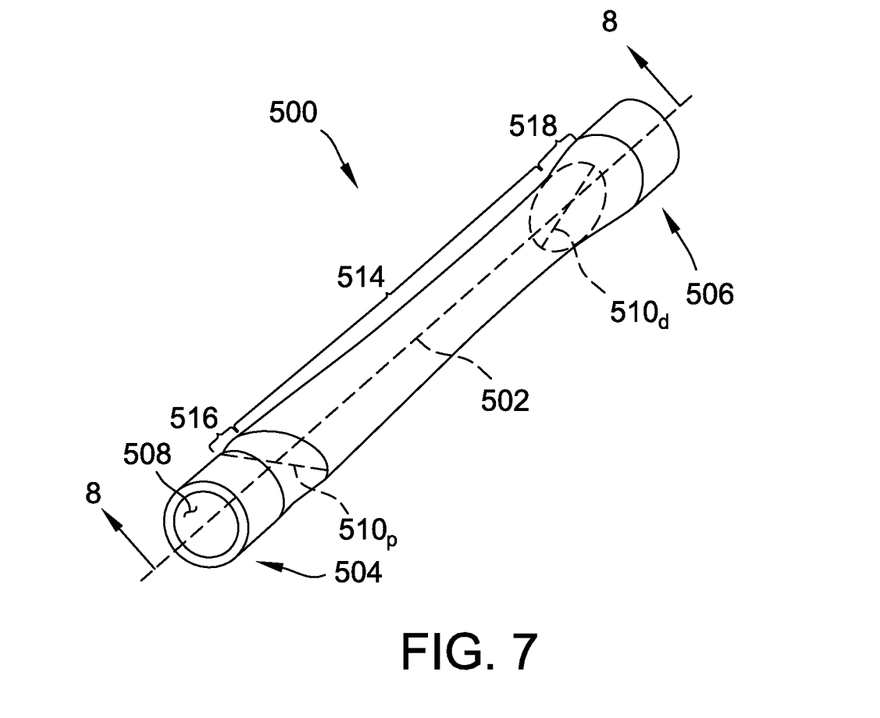
FIG. 7 is a perspective view of an exemplary support tube suitable for use with the electrode loop assembly shown in FIGS. 3-6.
Figure 8:
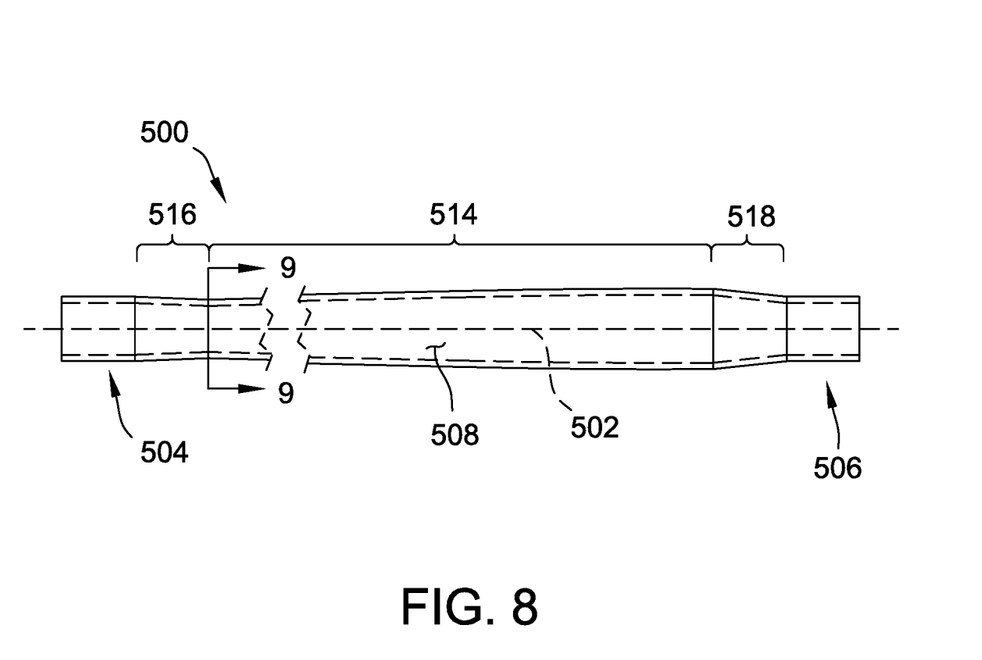
FIG. 8 is a cross-sectional view of the support tube of FIG. 7 taken along line "8-8" in FIG. 7.
Figure 9:
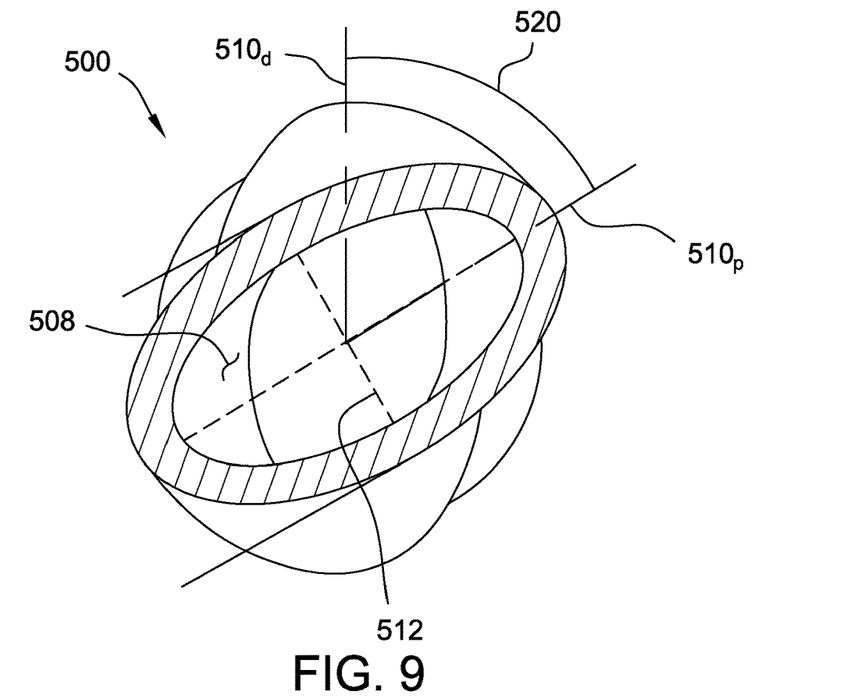
FIG. 9 is a cross-sectional view of the support tube of FIG. 7 taken along line "9-9" in FIG. 8.

FIG. 7 is a perspective view of an exemplary support tube 500 suitable for use with the electrode loop assemblies described herein, such as electrode loop assembly 300 (shown in FIGS. 3-6). FIG. 8 is a cross-sectional view of support tube 500 taken along line "8-8" in FIG. 7, and FIG. 9 is a cross-sectional view of support tube 500 taken along line "9-9" in FIG. 8. Support tube 500 is shown in a pre-assembled state in FIGS. 7-9 (i.e., prior to form wire 324 and activation wire 326 being inserted therethrough), and is thus not in the shape of a loop. When support tube 500 is incorporated into an electrode loop assembly, such as electrode loop assembly 300, a form wire and an activation wire (e.g., form wire 324 and activation wire 326) are routed through support tube 500, and support tube 500 assumes the shape of the electrode loop assembly provided by the form wire.

As shown in FIGS. 7-9, support tube 500 extends along a longitudinal axis 502 from a proximal end 504 to a distal end 506. Support tube 500 defines a lumen 508 that extends from proximal end 504 to distal end 506. When support tube 500 is implemented in an electrode loop assembly, a form wire and an activation wire (e.g., form wire 324 and activation wire 326) are routed through lumen 508 such that the form wire and activation wire are enclosed within support tube 500.

Support tube 500 has an oblong cross-section having a major dimension or axis 510 oriented perpendicular to longitudinal axis 502. As used herein, the major dimension or axis of a support tube refers to the largest dimension of the cross-section of the support tube as measured in a direction perpendicular to the longitudinal axis of the support tube. In the illustrated embodiment, support tube 500 has an elliptical cross-section, and the major axis 510 of the support tube corresponds to the major axis of the ellipse defined by the cross-section of support tube 500. Additionally, in the illustrated embodiment, elliptical cross-section of support tube 500 includes a minor axis 512 oriented perpendicular to both major axis 510 and longitudinal axis 502. In other embodiments, support tube 500 may have an oblong cross-section other than an elliptical cross-section, including, for example and without limitation, a pseudo-rectangular cross-section and an oval-shaped cross-section. In such embodiments, the cross-section of support tube 500 may not have a defined minor axis 512.

In the illustrated embodiment, the oblong cross-section of support tube 500 is defined along an intermediate portion 514 of support tube 500 that extends between proximal end 504 of support tube 500 and distal end 506 of support tube 500. Intermediate portion 514 extends less than the full length of support tube 500 such that the oblong cross-section is defined only along a portion of support tube 500 in the illustrated embodiment.

Further, in the illustrated embodiment, each of proximal end 504 and distal end 506 has a cross-section shaped differently than intermediate portion 514. Specifically, each of proximal end 504 and distal end 506 has a circular cross-section. The circular cross-section of proximal end 504 and distal end 506 may facilitate connecting support tube 500 to other, similarly-shaped components of a catheter in which support tube 500 is implemented.

Additionally, the illustrated support tube 500 includes transitional sections 516, 518 disposed between intermediate portion 514 and proximal end 504 and distal end 506, respectively. Transitional sections 516, 518 have a tapering cross-section that transitions from the cross-sectional shape of the respective proximal and distal ends 504, 506, to the cross-sectional shape of intermediate portion 514. Thus, in the illustrated embodiment, each transitional section 516, 518 tapers from a circular cross-section to an elliptical cross-section.

In other embodiments, the oblong cross-section of support tube 500 may extend to one or both of proximal end 504 and distal end 506, and/or extend the full length of support tube 500. In such embodiments, support tube 500 may not include transitional sections 516, 518, and one or both of proximal end 504 and distal end 506 may have the same cross-section (i.e., oblong) as the remainder of support tube 500.

As shown in FIGS. 7 and 9, support tube 500 is twisted about longitudinal axis 502 such that an orientation of major axis 510 changes along a length of support tube 500. In the illustrated embodiment, for example, support tube 500 is twisted in a counter-clockwise direction such that an orientation of major axis $510_d$ at the distal end of intermediate portion 514 is angularly offset from the major axis $510_p$ at the proximal end of intermediate portion 514 by an angle 520. In the illustrated embodiment, support tube 500 is twisted by an angle 520 of about 60° from the proximal end of intermediate portion 514 to the distal end of intermediate portion 514. That is, the orientation of major axis $510_d$ at the distal end of intermediate portion 514 is angularly offset from the major axis $510_p$ at the proximal end of intermediate portion 514 by an angle of about 60°. In other embodiments, support tube 500 may be twisted by any suitable angle 520 that enables support tube 500 to function as described herein. In some embodiments, for example, support tube 500 is twisted such that the orientation of major axis $510_d$ at the distal end of intermediate portion 514 is angularly offset from the major axis $510_p$ at the proximal end of intermediate portion 514 by an angle 520 of at least 0°, such as between 1° and 180°, between 5° and 180°, between 5° and 130°, between 5° and 90°, between 10° and 180°, between 10° and 130°, between 10° and 90°, between 20° and 180°, between 20° and 130°, or between 20° and 90°. Further, although support tube 500 is illustrated and described as being twisted in the counter-clockwise direction, it should be understood that support tube 500 may be twisted in the opposite, clockwise direction in other embodiments.

Further, in the illustrated embodiment, the orientation of major axis 510 continuously changes or rotates along intermediate portion 514 of support tube 500. That is, as intermediate portion 514 extends distally, orientation of major axis 510 continuously changes or rotates. In other embodiments, the orientation of major axis 510 may change in discrete, non-continuous segments.

The particular shape of support tube 500—namely, the twisted, oblong cross-sectional shape of support tube 500—facilitates maintaining the relative position of the activation wire and the form wire, and thereby facilitates maintaining the proper shape of electrode loop assemblies in which support tube 500 is implemented. In particular, when support tube 500 is implemented in an electrode loop assembly (e.g., electrode loop assembly 300), the twisted, oblong cross-sectional shape of support tube 500 inhibits the associated activation wire (e.g., activation wire 326) from moving radially past or outward from the associated form wire (e.g., form wire 324), and thereby confines the activation wire to the radial inner side of the form wire. Consequently, the support tubes of the present disclosure facilitate maintaining the proper shape of electrode loop assemblies and preventing loop misshaping.

Additionally, without being bound by any particular theory, it is believed that the direction in which support tube 500 is twisted relative to the direction in which the associated electrode loop assembly (e.g., electrode loop assembly 300) extends from the catheter shaft can further facilitate maintaining the proper shape of the electrode loop assembly and prevent loop misshaping. More specifically, support tubes twisted in the same direction or orientation in which the associated electrode loop assembly extends from the distal end of the catheter shaft (i.e., clockwise or counter-clockwise) have demonstrated superior performance, as compared to support tubes twisted in the opposite direction, in maintaining the proper shape of the electrode loop assembly and preventing loop misshaping.

In the embodiment illustrated in FIGS. 3-6, for example, electrode loop assembly 300 extends from distal end 402 of catheter shaft 400 in a counter-clockwise direction (i.e., when viewed from the proximal end of catheter shaft 400). Accordingly, in at least some embodiments, using a support tube with a counter-clockwise twist may provide improved performance as compared to a support tube with a clockwise twist. Conversely, in embodiments where the electrode loop assembly extends from the distal end of the catheter shaft in a clockwise direction (i.e., when viewed from the proximal end of the catheter shaft), using a support tube with a clockwise twist may provide improved performance as compared to a support tube with a counter-clockwise twist.

Support tube 500 may be formed using any suitable apparatus and techniques known in the art, including, for example and without limitation, rollers, mandrels, presses, plates, and combinations thereof. In one exemplary embodiment, support tube 500 is formed by compressing a cylindrical piece of material (e.g., a braided polyimide tube) between a roller and a press plate such that the cylindrical piece of material is formed to have an oblong cross-section, and subsequently imparting a rotational twist along a length of the piece of material using a rotational fixture.

Figure 10:
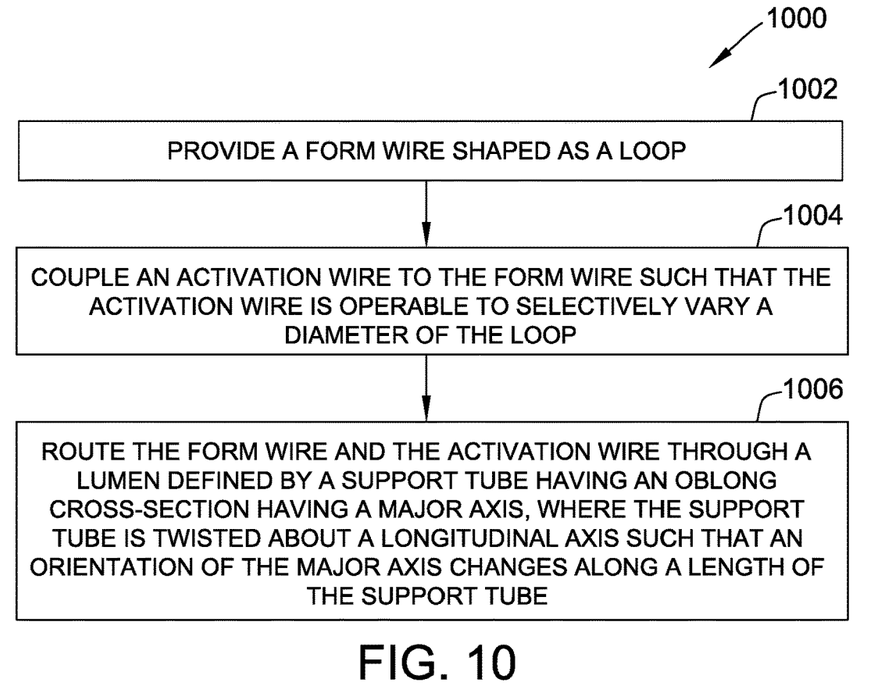
FIG. 10 is a flow diagram illustrating one embodiment of a method of assembling an electrode loop assembly.

FIG. 10 is a flow diagram illustrating one embodiment of a method 1000 of assembling an electrode loop assembly, such as electrode loop assembly 300 shown in FIGS. 3-6. In the illustrated embodiment, the method 1000 includes providing 1002 a form wire (e.g., form wire 324) shaped as a loop, and coupling 1004 an activation wire (e.g., activation wire 326) to the form wire such that the activation wire is operable to selectively vary a diameter of the loop, and the activation wire is routed along a radial inner side of the form wire. The method further includes routing 1006 the form wire and the activation wire through a lumen defined by a support tube (e.g., support tube 500) that has an oblong cross-section having a major axis and is twisted about a longitudinal axis such that an orientation of the major axis changes along a length of the support tube.

Although certain steps of the example method are numbered, such numbering does not indicate that the steps must be performed in the order listed. Thus, particular steps need not be performed in the exact order they are presented, unless the description thereof specifically require such order. The steps may be performed in the order listed, or in another suitable order.

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

This written description uses examples to disclose the invention, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An electrode loop assembly for a catheter, said electrode loop assembly comprising:
   a form wire shaped as a loop;
   an activation wire coupled to the form wire and operable to selectively vary a diameter of the loop, the activation wire routed along a radial inner side of the form wire; and
   a support tube defining a lumen and enclosing the form wire and the activation wire therein, wherein the support tube extends along a longitudinal axis from a proximal end to a distal end, wherein the support tube has an oblong cross-section having a major axis, and wherein the support tube is twisted about the longitudinal axis such that an orientation of the major axis changes along a length of the support tube.

2. The electrode loop assembly of claim 1, wherein the support tube confines the activation wire to the radial inner side of the form wire.

3. The electrode loop assembly of claim 1, wherein the support tube is twisted counter-clockwise.

4. The electrode loop assembly of claim 1, wherein the support tube is twisted clockwise.

5. The electrode loop assembly of claim 1, wherein the oblong cross-section is defined along an intermediate portion of the support tube extending between the proximal end of the support tube and the distal end of the support tube, wherein the major axis at a distal end of the intermediate portion is angularly offset from the major axis at a proximal end of the intermediate portion by an angle of greater than 0°.

6. The electrode loop assembly of claim 5, wherein the major axis at the distal end of the intermediate portion is angularly offset from the major axis at the proximal end of the intermediate portion by an angle of between 1° and 180°.

7. The electrode loop assembly of claim 5, wherein each of the proximal end and the distal end of the support tube has a circular cross-section.

8. The electrode loop assembly of claim 1, wherein the support tube is constructed from at least one of braided material, coiled wire, and combinations thereof.

9. The electrode loop assembly of claim 1, wherein the support tube has an oval-shaped cross-section.

10. The electrode loop assembly of claim 1, wherein the support tube has an elliptical cross-section.

11. The electrode loop assembly of claim 1, wherein the support tube has a pseudo-rectangular cross-section.

12. The electrode loop assembly of claim 1, wherein the form wire is constructed from a memory-shape material.

13. The electrode loop assembly of claim 1, wherein the activation wire is coupled to the form wire at a distal tip thereof.

14. The electrode loop assembly of claim 1 further comprising:
   an outer sleeve defining an outer lumen, wherein the form wire, the activation wire, and the support tube extend through the outer lumen; and
   a plurality of electrodes coupled to the outer sleeve.

15. A catheter assembly comprising:
   a catheter shaft extending from a proximal end to a distal end;

a handle coupled to the catheter shaft at the proximal end thereof and including a loop actuator; and an electrode loop assembly coupled to the catheter shaft at the distal end thereof, the electrode loop assembly including:

a form wire shaped as a loop;

an activation wire coupled to the form wire and the loop actuator, wherein the activation wire is operable to selectively vary a diameter of the loop upon actuation of the loop actuator, the activation wire routed along a radial inner side of the form wire; and a support tube defining a lumen and enclosing the form wire and the activation wire therein, wherein the support tube extends along a longitudinal axis from a proximal end to a distal end, wherein the support tube has an oblong cross-section having a major axis, and wherein the support tube is twisted about the longitudinal axis such that an orientation of the major axis changes along a length of the support tube.

16. The catheter assembly of claim 15, wherein the electrode loop assembly extends from the distal end of the catheter shaft in a counter-clockwise direction, and wherein the support tube is twisted counter-clockwise.

17. The catheter assembly of claim 15, wherein the electrode loop assembly extends from the distal end of the catheter shaft in a clockwise direction, and wherein the support tube is twisted clockwise.

18. The catheter assembly of claim 15, wherein the oblong cross-section is defined along an intermediate portion of the support tube extending between the proximal end of the support tube and the distal end of the support tube, wherein the major axis at a distal end of the intermediate portion is angularly offset from the major axis at a proximal end of the intermediate portion by an angle of greater than 0°.

19. The catheter assembly of claim 18, wherein the major axis at the distal end of the intermediate portion is angularly offset from the major axis at the proximal end of the intermediate portion by an angle of between 1° and 180°.

20. A method of assembling an electrode loop assembly, said method comprising:

providing a form wire shaped as a loop;

coupling an activation wire to the form wire such that the activation wire is operable to selectively vary a diameter of the loop, wherein the activation wire is routed along a radial inner side of the form wire; and routing the form wire and the activation wire through a lumen defined by a support tube, wherein the support tube defines a longitudinal axis and has an oblong cross-section having a major axis, and wherein the support tube is twisted about the longitudinal axis such that an orientation of the major axis changes along a length of the support tube.

* * * * *